(12) United States Patent
Warren et al.

(10) Patent No.: US 10,827,974 B2
(45) Date of Patent: Nov. 10, 2020

(54) PREDICTING WEIGHT LOSS AND FAT METABOLISM USING OPTICAL SIGNAL CHANGES IN FAT

(71) Applicant: The Regents of the University of California, Oakland, CA (US)

(72) Inventors: Robert Warren, Irvine, CA (US); Goutham Ganesan, Irvine, CA (US); Thomas O'Sullivan, Laguna Hills, CA (US); Shaista Malik, Orange, CA (US); Bruce J. Tromberg, Irvine, CA (US); Pietro Galassetti, Washington, DC (US)

(73) Assignee: The Regents of the University of California, Oakland, CA (US)

( * ) Notice: Subject to any disclaimer, the term of this patent is extended or adjusted under 35 U.S.C. 154(b) by 599 days.

(21) Appl. No.: 15/411,674

(22) Filed: Jan. 20, 2017

(65) Prior Publication Data
US 2017/0209089 A1    Jul. 27, 2017

Related U.S. Application Data

(60) Provisional application No. 62/286,209, filed on Jan. 22, 2016.

(51) Int. Cl.
*A61B 5/00* (2006.01)
*A61B 5/1455* (2006.01)
(Continued)

(52) U.S. Cl.
CPC ........ *A61B 5/4872* (2013.01); *A61B 5/14546* (2013.01); *A61B 5/14551* (2013.01);
(Continued)

(58) Field of Classification Search
CPC .................................................. A61B 5/4872
(Continued)

(56) References Cited

U.S. PATENT DOCUMENTS

| | | | | |
|---|---|---|---|---|
| 7,711,411 B2* | 5/2010 | Azizian | ............... | A61B 5/0059 250/339.02 |
| 2007/0282179 A1* | 12/2007 | Merritt | ................ | A61B 5/0059 600/315 |

(Continued)

FOREIGN PATENT DOCUMENTS

WO    WO-2014113333 A1 *  7/2014  .......... A61B 5/0075

OTHER PUBLICATIONS

Leitner, Brooks P., Mapping of human brown adipose tissue in lean and obese young men, Proceedings of the National Academy of Sciences of the United States of America, Aug. 8, 2017, 8649-8654, vol. 114, No. 32.

*Primary Examiner* — Lynsey C Eiseman
(74) *Attorney, Agent, or Firm* — Marcus C. Dawes; Daniel L. Dawes

(57) ABSTRACT

A quantitative, non-invasive optical spectroscopy technique for measuring dynamic changes in adipose tissue structure and metabolism in vivo. The technique requires multiple wavelengths of light in the near-infrared (650-1000 nm). Using these wavelengths of light, adipose tissue is illuminated and light that returns to a photodetector is analyzed. From the return signals, the absorption and reduced scattering coefficients ($\mu_a$ and $\mu_s'$) at each wavelength are calculated. The obtained $\mu_a$ and $\mu_s'$ values allow for quantification of biomarkers and indices which allow for measurement of fat composition and metabolism. The concentration of oxy- and deoxy-hemoglobin, the fractional water and lipid content, and information about the size distribution of light scatterers in the adipose tissue are also determined. A detailed and quantitative understanding of fat composition (Continued)

and metabolism is thereby provided which describes the effectiveness of interventions to improve the health of a patient.

**10 Claims, 7 Drawing Sheets
(2 of 7 Drawing Sheet(s) Filed in Color)**

(51) Int. Cl.
*A61B 5/145* (2006.01)
*G16H 50/20* (2018.01)

(52) U.S. Cl.
CPC .......... *A61B 5/4875* (2013.01); *A61B 5/6823* (2013.01); *A61B 5/7275* (2013.01); *A61B 5/743* (2013.01); *G16H 50/20* (2018.01)

(58) Field of Classification Search
USPC .................................. 600/309–310; 128/921
See application file for complete search history.

(56) References Cited

U.S. PATENT DOCUMENTS

| | | | | |
|---|---|---|---|---|
| 2008/0103698 | A1* | 5/2008 | Bae | A61B 5/4872 |
| | | | | 702/1 |
| 2009/0024013 | A1* | 1/2009 | Soller | A61B 5/14551 |
| | | | | 600/324 |
| 2015/0351635 | A1* | 12/2015 | Cerussi | A61B 5/0075 |
| | | | | 600/477 |
| 2016/0003612 | A1* | 1/2016 | Cirillo | G06F 3/01 |
| | | | | 348/47 |
| 2016/0220183 | A1* | 8/2016 | Hamaoka | A61B 5/1455 |

* cited by examiner

PREDICTING WEIGHT LOSS AND FAT METABOLISM USING OPTICAL SIGNAL CHANGES IN FAT

GOVERNMENT SUPPORT

This invention was made with government support under grants EB015890 and TR000153 awarded by the National Institutes of Health. The government has certain rights in the invention.

BACKGROUND

Field of the Technology

The invention relates to the field of medical diagnostic and biomedical optics and specifically relates to weight loss: a non-invasive, optical method to monitor and predict the effectiveness of weight loss interventions by measuring fat composition and metabolism.

Description of the Prior Art

Recent physiological studies have revealed the potentially critical role of adipose tissue (AT) in the development of metabolic disorders. Both visceral and subcutaneous AT have been shown to be subject to various pathophysiological processes, such as inflammation, dysregulated oxygenation, and disrupted endocrine signaling. Despite the importance of AT in disease, there are no widely-used clinical methods for assessing AT physiology in humans. In other words, there are no easily accessible, non-invasive tools available to measure changes in fat (adipose tissue) structure or function, which can provide indications of the progress of weight loss intervention and other pathologies associated with adipocyte size and metabolism such as insulin resistance and vascular dysfunction. Recent investigations have established a clear role for changes in adipocyte size and oxygen metabolism in driving the early stages of pathologies such as insulin resistance and vascular dysfunction. However, there are no diagnostic tools available to assess tissue structure or function in fat tissue in vivo.

The currently proposed solutions include ultrasound and optical techniques to monitor the macro-structure of adipose tissue during interventions. Ultrasound techniques provide tomographic imaging of biological tissue which allows the thickness of various layers of tissue to be quantified. Optical techniques have been described (patent numbers JP2002191578-A & JP4547804-B2) which also quantify fat layer thickness.

These techniques have certain disadvantages and limitations, namely existing technologies are sensitive only to changes in macro-structure of adipose tissue layers, such as the thickness. None of them are capable of measuring changes reflective of cell size, metabolism, or extracellular milieu, which occur prior to changes in the macro-structure.

Given the potential importance of the AT in metabolic disease, there is a need for new measurement tools to characterize and image it. Diffuse Optical Spectroscopic Imaging (DOSI) may be uniquely suited to this purpose. DOSI quantitatively measures interactions of near-infrared light with tissues at depth. DOSI measurements of tissue reduced scattering ($\mu_s'$) and absorption ($\mu_a$) coefficients are used to calculate tissue concentrations of oxyhemoglobin [$HbO_2$], deoxyhemoglobin [HbR], water, and bulk lipid fractions, which together indirectly reflect aspects of tissue perfusion, metabolism, hydration and total blood volume. Diffuse optical techniques are increasingly used in the study of cerebral and muscular hemodynamics and metabolism, as well as in cancer biology, but to this date they have not been explored for measuring AT.

BRIEF SUMMARY

Changes in subcutaneous adipose tissue (AT) structure and metabolism have been shown to correlate with the development of obesity and related metabolic disorders. We have developed a novel use of an emerging functional imaging technology, Diffuse Optical Spectroscopic Imaging (DOSI), for monitoring these changes in subcutaneous AT structure and metabolism during weight loss. Our technique utilizes near-infrared light to non-invasively monitor AT optical and physiological properties. As individuals lose weight, our technique senses changes in light scattering properties, blood, water, fat, and oxygen utilization. Optical scattering signals reveal alterations in tissue structure consistent with changes in adipose cells that accompany weight loss, while water and hemoglobin dynamics suggest improved AT perfusion and oxygen extraction, consistent with metabolic changes in AT that can be used to monitor and predict the effectiveness of weight loss regimens. In summary, our technique provides feedback for patients and clinicians regarding the effectiveness of weight loss interventions.

Recently, we utilized DOSI to obtain quantitative measures of near infrared (NIR) AT optical and physiological properties in 10 overweight adults during a three-month calorie-restricted diet. Calorie restriction, or CR, has been shown to extend life span and reduce incidence of obesity-related complications in mammals, and these effects are mediated in part by changes in AT. In mice, three months of CR can lead to nitric oxide (NO) mediated increases in white AT mitochondrial DNA, peroxisome proliferator-activated receptor-γ coactivator 1α (PGC-1α), and markers of mitochondrial biogenesis. It is suggested that enhanced white AT SIRTO expression contributes to the pro-longevity effects of CR in mammals. Specifically, studies of CR in humans have reported morphological changes in AT, such as adpipocyte size changes and altered profile of inflammatory cells. Weight reduction by CR leads to adipocyte shrinkage and it has been shown that a 10% weight loss results in a 16% decrease in adipocyte volume, whereas a high-fat diet increases adipocyte volume in a matter of weeks. In humans, a strong positive correlation has been found between adipocyte size and the presence of type 2 Diabetes or its associated risk factors in bariatric surgery candidates. Another recent study revealed a correlation between adipocyte hypertrophy and both insulin resistance and AT inflammation.

It is also possible that adipocyte size changes influence cellular metabolism. For example, some data suggest a relationship between adipocyte size and AT angiogenesis. More important is the hypothesized relationship between adipocyte size and $O_2$ delivery. The diameters of hypertrophic adipocytes are thought to exceed the diffusion distance of $O_2$, causing lower cellular $P_{O2}$. This cellular hypoxia has been observed as a feature of AT in obesity in most studies, but there are some conflicting reports. Most importantly, there are data to suggest that it is increased AT $P_{O2}$ that is associated with inflammation and insulin resistance in obesity. A recent investigation in mice found that expression of hypoxia-inducible factor (HIF)-1 alpha increased in animals fed a high-fat diet, in response to increased AT $O_2$ consumption. Other lines of investigation have focused on the characterization of "beige" adipocytes, which tend to consume more $O_2$ and are thought to correlate with enhanced metabolic health.

DOSI derived tissue concentrations of hemoglobin, water, and lipid and the wavelength-dependent scattering amplitude (A) and slope (b) obtained from 30 abdominal locations and three time points were calculated and analyzed using linear mixed effects models, and were also used to form three dimensional surface images. Subjects lost a mean of 11.7±3.4% of starting weight, while significant changes in A, b, tissue water fraction and deoxyhemoglobin [HbR] were observed. Optical scattering signals reveal alterations in tissue structure consistent with reductions in adipose cell volume, while water and hemoglobin dynamics suggest improved AT perfusion and oxygen extraction, consistent with possible "browning" of AT. These results suggest that DOSI measurements of NIR optical properties could be used to enhance understanding of the role of AT in disease progression, and to advance diagnostics and monitoring of metabolic disorders.

The current invention includes an improvement in a method for measuring dynamic changes in adipose tissue metabolism in vivo in a patient during a weight loss treatment. The improvement includes identifying a plurality of test points on the abdominal region of a patient, generating a diffuse optical spectroscopic image (DOSI) using near-infrared light at each of plurality of test points, and generating a measurement of tissue reduced scattering ($\mu_s'$) and absorption ($\mu_a$) coefficients at each of the plurality of test points in the diffuse optical spectroscopic image (DOSI). The improvement further includes calculating the concentrations of a plurality chromophores from the obtained tissue absorption coefficient and reduced scattering coefficient from the measured tissue reduced scattering ($\mu_s'$) and absorption ($\mu_a$) coefficients at each of the plurality of test points in the diffuse optical spectroscopic image (DOSI). Additionally, the improvement includes repeating at intervals during the weight loss treatment the steps of identifying a plurality of test points on the abdominal region of a patient, generating a diffuse optical spectroscopic image (DOSI) using near-infrared light at each of plurality of test points, generating a measurement of tissue reduced scattering ($\mu_s'$) and absorption ($\mu_a$) coefficients at each of the plurality of test points in the diffuse optical spectroscopic image (DOSI), calculating tissue concentrations of oxyhemoglobin [$HbO_2$], deoxyhemoglobin [HbR], water, and bulk lipid fractions from the measured tissue reduced scattering ($\mu_s'$) and absorption ($\mu_a$) coefficients at each of the plurality of test points in the diffuse optical spectroscopic image (DOSI) to monitor changes in subcutaneous adipose tissue structure and metabolism during weight loss through use of near-infrared light to non-invasively monitor adipose tissue optical and physiological properties. In one particular embodiment, changes in light scattering properties of blood, water, fat, and oxygen utilization are used to indicate alteration in tissue structure consistent with changes in adipose tissue that accompany weight loss, while water and hemoglobin dynamics indicate improved adipose tissue perfusion and oxygen extraction, consistent with metabolic changes in adipose tissue to monitor and predict the effectiveness of weight loss regimens.

In one embodiment, the method step of generating a diffuse optical spectroscopic image (DOSI) using near-infrared light at each of the plurality of test points includes placing a photodetector and a multiple of light source fibers to provide a corresponding multiple wavelengths of light in the near-infrared (650-1000 nm) at each of the plurality of test points.

In a separate embodiment, the method step of generating a diffuse optical spectroscopic image (DOSI) using near-infrared light at each of plurality of test points includes combining frequency-dependent photo migration (FDPM) imaging at a plurality of discrete wavelengths with broadband diffuse reflectance spectroscopy (DRS) to determine broadband absorption and scattering to allow for calculation of concentrations of chromophores in tissue at the plurality of test points. This embodiment further includes combining frequency-dependent photo migration (FDPM) imaging at a plurality of discrete wavelengths with broadband diffuse reflectance spectroscopy (DRS) to determine broadband absorption and scattering to allow for calculation of concentrations of chromophores in tissue at the plurality of test points comprises combining the measured values obtained from the frequency-dependent photo migration (FDPM) imaging with the measured values obtained from broadband diffuse reflectance spectroscopy (DRS) to determine a tissue absorption coefficient ($\mu_a$) and a reduced scattering coefficient ($\mu_s'$) over a wavelength spectrum for each of the plurality of test points including 650-1000 nm. Additionally, the embodiment further includes obtaining an oxygen saturation ($StO_2$) and a tissue optical index (TOI) related to the patient, wherein the oxygen saturation is the ratio of oxyhemoglobin to total hemoglobin, and wherein the tissue optical index is the product of the water fraction and deoxyhemoglobin divided by the lipid fraction, the oxygen saturation and tissue optical index representing an index of metabolic activity of the patient.

In yet another embodiment, the method step of generating a diffuse optical spectroscopic image (DOSI) using near-infrared light at each of plurality of test points includes plotting DOSI data at grid coordinates corresponding to the plurality of test points, using a heat map function to interpolate onto a map including the grid coordinates, and overlaying the map onto a three dimensional textured mesh of a representative abdomen of a patient to create a processed image.

In another embodiment, the method step of calculating the concentrations of a plurality chromophores from the obtained tissue absorption coefficient and reduced scattering coefficient comprises calculating concentrations of oxyhemoglobin ($HbO_2$), deoxyhemoglobin (HbR), total hemoglobin (THb), and fractions of water content and lipid content. This method may also include obtaining an oxygen saturation ($StO_2$) and a tissue optical index (TOI) related to the patient, wherein the oxygen saturation is the ratio of oxyhemoglobin to total hemoglobin, and wherein the tissue optical index is the product of the water fraction and deoxyhemoglobin divided by the lipid fraction, the oxygen saturation and tissue optical index representing an index of metabolic activity of the patient.

In yet another embodiment, the improved method also includes correlating the determined tissue absorption coefficient ($\mu_a$) and reduced scattering coefficient ($\mu_s'$) to a higher density and a reduced volume of adipose tissue within the patient. Here, correlating the determined tissue absorption coefficient ($\mu_a$) and reduced scattering coefficient ($\mu_s'$) to a higher density and a reduced volume of adipose tissue within the patient may include guiding therapeutic interventions including diet, exercise, and medication by assessing their impact on the adipose tissue within the patient. Alternatively, correlating the determined tissue absorption coefficient ($\mu_a$) and reduced scattering coefficient ($\mu_s'$) to a higher density and a reduced volume of adipose tissue within the patient may include correlating the tissue absorption coefficient ($\mu_a$) and reduced scattering coefficient ($\mu_s'$) with improvements in vascular disease risk observed in the patient.

The invention further provides for an improvement in a method for measuring dynamic changes in adipose tissue metabolism in vivo in a patient. The improved method includes applying frequency-dependent photon migration (FDPM) at each of a plurality of test points on the abdomen of the patient, applying broadband near-infrared spectroscopy (NIRS) at each of the plurality of test points, and combining the measured values obtained from the FDPM with the measured values obtained from the broadband NIRS to determine a tissue absorption coefficient ($\mu_a$) and a reduced scattering coefficient ($\mu_s'$) over a wavelength spectrum for each of the plurality of test points. The improved method further includes plotting the combined FDPM and NIRS measured values using a plurality of grid coordinates to create a colored heat map representing a concentration of one of a plurality chromophores obtained from the tissue absorption coefficient and reduced scattering coefficient.

In one embodiment, the improved method further includes overlaying the heat map on a three dimensional textured mesh representing an abdomen of the patient, the combined heat map and three dimensional textured mesh showing the concentration of one of the plurality of chromophores relative to a location on the patient's abdomen.

In a separate embodiment, the colored heat map representing a concentration of one of a plurality chromophores obtained from the tissue absorption coefficient and reduced scattering coefficient represents a concentration of oxyhemoglobin (Hb02), deoxyhemoglobin (HbR), total hemoglobin (THb), a fraction of water content, or a fraction of lipid content.

In another embodiment, the method step of combining the measured values obtained from the FDPM with the measured values obtained from the broadband NIRS to determine a tissue absorption coefficient ($\mu_a$) and a reduced scattering coefficient ($\mu_s'$) over a wavelength spectrum for each of the plurality of test points includes obtaining the tissue absorption coefficient $\mu_a$ and reduced scattering coefficient $\mu_s'$ over a wavelength spectrum of 650-1000 nm.

In yet another embodiment, the method step of applying frequency-dependent photon migration (FDPM) at each of a plurality of test points on the abdomen of the patient and applying broadband near-infrared spectroscopy (NIRS) at each of the plurality of test points includes obtaining three measurements using FDPM and using NIRS at each of the plurality of test points and calculating an average measurement value for each of the plurality of test points.

In a further embodiment, the method step of combining the measured values obtained from the FDPM with the measured values obtained from the broadband NIRS to determine a tissue absorption coefficient ($\mu_a$) and a reduced scattering coefficient ($\mu_s'$) over a wavelength spectrum for each of the plurality of test points includes calculating the tissue absorption and reduced scattering coefficients from a measured phase and amplitude of a detected light using calibration on a silicone phantom of known optical properties.

In another embodiment, the improved method also includes correlating the created heat map representing a concentration of one of a plurality chromophores obtained from the tissue absorption coefficient and reduced scattering coefficient to a higher density and a reduced volume of adipose tissue within the patient. Here, correlating the created heat map representing a concentration of one of a plurality chromophores obtained from the tissue absorption coefficient and reduced scattering coefficient to a higher density and a reduced volume of adipose tissue within the patient may include guiding therapeutic interventions including diet, exercise, and medication by assessing their impact on the adipose tissue within the patient. Alternatively, correlating the created heat map representing a concentration of one of a plurality chromophores obtained from the tissue absorption coefficient and reduced scattering coefficient to a higher density and a reduced volume of adipose tissue within the patient may include correlating the created heat map with improvements in vascular disease risk observed in the patient.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The disclosure can be better visualized by turning now to the following drawings wherein like elements are referenced by like numerals.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Figure 1:
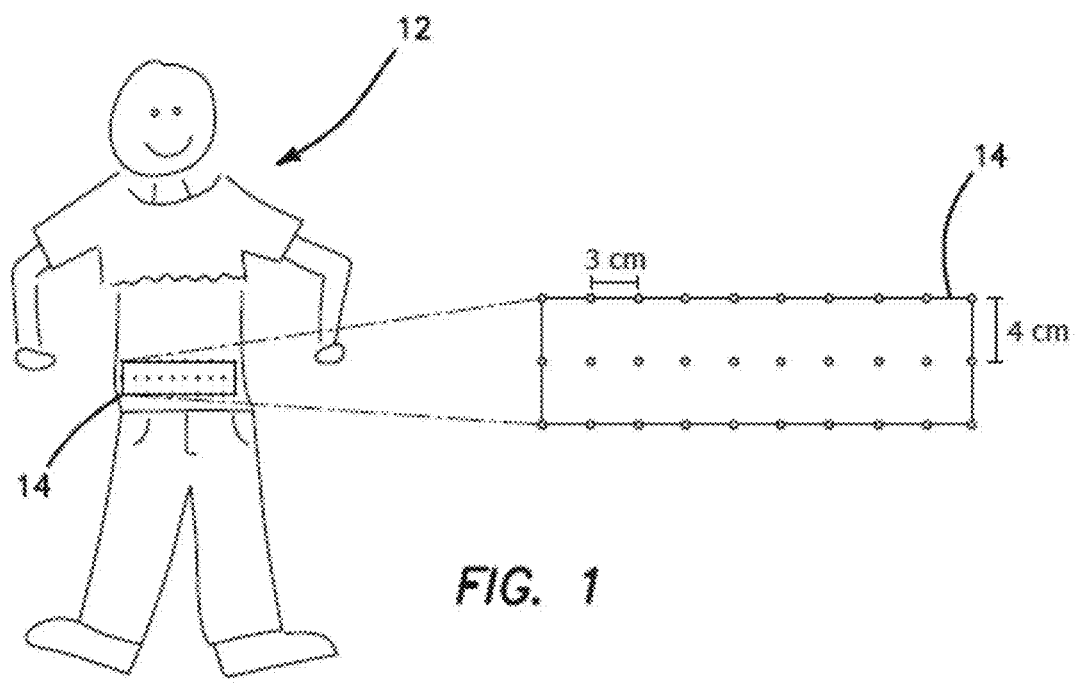
FIG. 1 is a schematic representation of a DOSI sample grid placed on a subject.

The patent or application file contains at least one drawing executed in color. Copies of this patent or patent application publication with color drawing(s) will be provided by the Office upon request and payment of the necessary fee.

DETAILED DESCRIPTION OF THE PREFERRED EMBODIMENTS

Method Overview

We are presenting for the first time the use of a quantitative, non-invasive optical spectroscopy technique for measuring dynamic changes in AT structure and metabolism in vivo. Our technique requires multiple wavelengths of light in the near-infrared (650-1000 nm). Using these wavelengths of light, we illuminate adipose tissue and analyze light that returns to a photodetector. Our analysis of the return signals allows for the calculation of absorption and reduced scattering coefficients ($\mu_a$ and $\mu_s'$) at each wavelength. The obtained $\mu_a$ and $\mu_s'$ values allow for quantification of biomarkers and indices which allow us to measure fat composition and metabolism. For example, we are able to determine the concentration of oxy- and deoxy-hemoglobin, the fractional water and lipid content, and information about the size distribution of light scatterers in the adipose tissue. We are not limited to this information, however, and our technique is sensitive to any unique absorbers or scatterers of light we shine into tissue. Since our technique reveals a detailed and quantitative understanding of fat composition and metabolism, we are able to describe the effectiveness of interventions to improve health.

Clinical Validation

We have applied a specific form of this technology to study the response of AT to calorie restriction (CR), an intervention known to produce significant improvements in weight and health. Our data demonstrate that DOSI-detected changes in optical and physiological properties are consistent with existing hypotheses on the response of AT to CR and weight loss.

In our clinical study, participants were recruited from a medically-supervised weight management program. Males and females 18-75 years old were included. Measurement sessions occurred three times: T0 (before or within two weeks of starting weight loss), T6 (6-8 weeks after T0), and T12 (6 weeks after T6). At each measurement session, subjects were assessed for weight, blood pressure, abdominal circumference, diet and physical activity. Blood pressure was obtained while supine, after ten minutes of rest. A total of 11 subjects participated in this study, of which one subsequently withdrew voluntarily, resulting in an n=10 (5 M, 5 F). Subsequent measurement sessions took place at the same time of day as the initial, and subjects were instructed to maintain the same daily schedule on subsequent measurement days with regard to meal timing and physical activity.

Weight loss was achieved through medically supervised calorie restriction by meal replacement (HMR 70 program, MA, USA). Two levels of calorie restriction were administered in this group of subjects according to subject preference. The more restrictive plan (type 1) involved intake of between 500-800 kcal/day, while the more flexible plan (type 2) allowed for up to 1200 kcal/day. Physical activity during the program was not controlled, but regular low to moderate exertion was encouraged. The rates of weight loss experienced therefore varied between subjects, as did the initial degree of overweight.

DOSI combines frequency-dependent photon migration (FDPM) with broadband diffuse reflectance spectroscopy (DRS). FDPM by itself can only be performed at discrete wavelengths (e.g., 790 nm, 830 nm) and is therefore limited in spectral resolution. Broadband DRS, on the other hand, offers good spectral resolution, but is by itself not quantitative because it ignores the contribution of tissue scattering. When the two modalities are combined, broadband absorption and scattering features can be determined which allow for calculation of concentrations of chromophores (e.g. oxy- and deoxy-hemoglobin, water, lipid) in a variety of human tissues.

Ultrasound images were taken and saved at each of the 10 middle row grid points using an HDI-5000 imaging unit (Phillips Healthcare, MA, USA). Subsequently, subcutaneous tissue thickness was measured and recorded using the embedded distance function of the device. Tissue thickness was defined as the distance from the surface of the skin to the most superficial visible muscle layer. Thickness values were recorded and analyzed for the middle row of DOSI grid positions at all three measurement sessions. Based on ultrasound measurements, Virtual Photonics software was used to conduct a Monte-Carlo simulation to assess theoretical photon penetration depth in AT.

Our data demonstrate that DOSI-detected changes in optical and physiological properties are consistent with existing hypotheses on the response of AT to CR and weight loss. Briefly, DOSI consists of two parallel optical measurement modalities, namely a combination of frequency-dependent photon migration (FDPM) with broadband NIRS. FDPM by itself can only be done at discrete wavelengths (e.g., 790 nm, 830 nm) and is therefore limited in spectral resolution. Additionally, FDPM uses modulated laser sources (50-500 MHz). Broadband NIRS, on the other hand, makes use of a white light source and a spectrophotometer to provide 650-1000 nm broadband reflectance data and offers good spectral resolution, but is by itself not quantitative because it ignores the contribution of tissue scattering. When the FDPM and NIRS signals are combined using a model-based approach to obtain quantitative tissue NIR absorption and scattering spectra, broadband absorption and scattering features can be determined which allow for calculation of concentrations of chromophores (e.g. oxy- and deoxy-hemoglobin, water, lipid) in a variety of human tissues.

According to the current method, subjects 12 were placed in a supine position and a skin marker was used to draw a rectangular grid 14 of thirty (30) points centered about the umbilicus. The grid 14 comprises three horizontal rows separated by 4 cm, and ten columns separated by 3 cm as depicted in FIG. 1. Before DOSI measurements were initiated, subjects were resting in a supine position for a minimum of ten minutes. At each point on the grid 14, three DOSI measurements were obtained and averaged for analysis. Grid points were named by row (U for upper, M for middle, L for lower), and column (1-10).

In one particular embodiment, DOSI is applied as follows. Detector and source fibers in a single silicone housing were placed on the surface of the skin at a source-detector separation of 22 mm. At each measurement point on the grid 14, reflected signals were collected, and analyzed using custom software in MATLAB (Mathworks, MA, USA). Tissue absorption ($\mu_a$) and reduced scattering ($\mu_s'$) coefficients were calculated from measured phase and amplitude of reflected modulated light using calibration on a silicone phantom of known optical properties. Then, broadband reflectance signal was fit to the measured FDPM optical properties to obtain $\mu_a$ and $\mu_s'$ at all wavelengths from 650-1000 nm. Finally, using published molar extinction coefficients, concentrations of oxyhemoglobin ([Hb0$_2$]), deoxyhemoglobin ([HbR]), total hemoglobin ([THb]), and fractions of water and lipid were calculated. From these quantities, the oxygen saturation (st0$_2$) and tissue optical index (TOI) were also calculated. The st0$_2$ is the ratio of [Hb0$_2$]/[THb]. TOI is the product of water fraction and [HbR], divided by lipid fraction, and serves as an index of metabolic activity.

Figure 2:
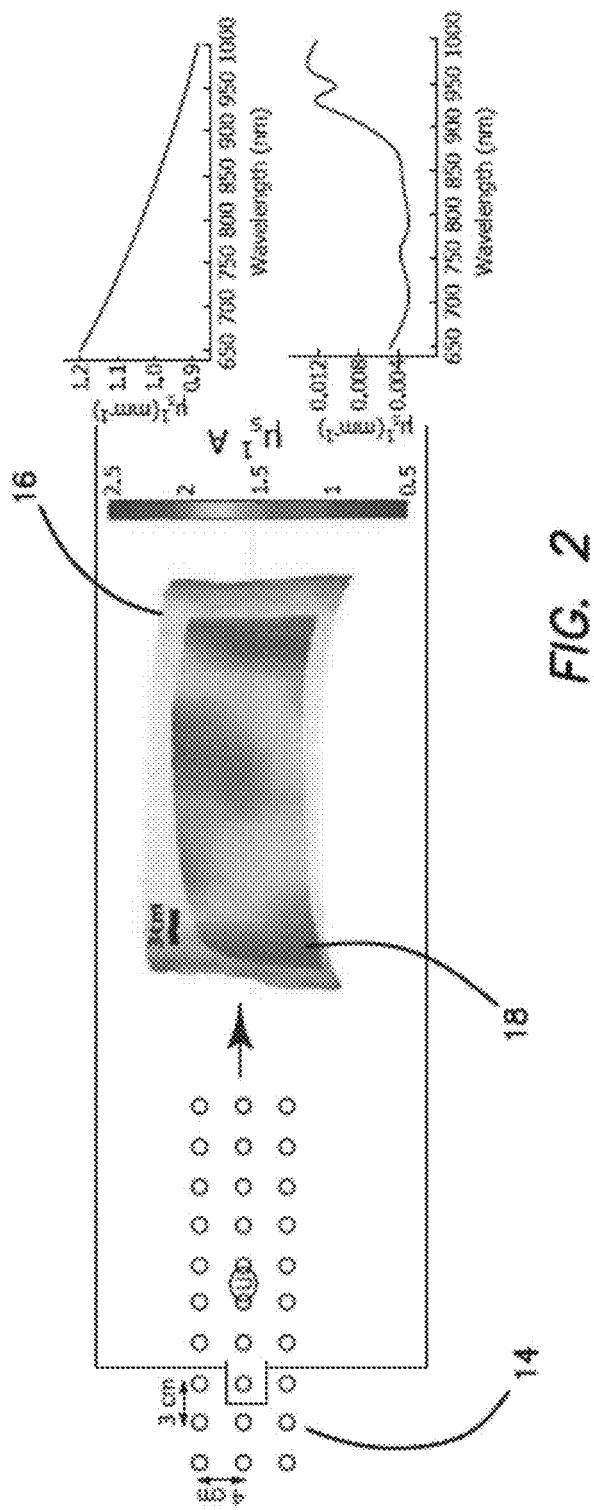
FIG. 2 is a schematic of the DOSI measurement procedure and shows the grid used with distances between points indicated along with a typical scattering spectrum obtained from one subject at a single point, with the mean of three replicate measurements shown as a line and a shaded area respectively.

At each measurement site of the grid 14 on the abdomen of the specimen 12, three measurements were obtained and averaged for analysis. After initial processing, DOSI data from each session was plotted using grid coordinates and heat map functions in MATLAB. Linear interpolation was used to account for sparse spacing of grid points. The colored maps 18 were then overlayed on a three dimensional textured mesh of a one representative abdomen 16 with grid points drawn on it. The initial three dimensional image was obtained by using Kinect for windows and accompanying software development kit (Microsoft, WA, USA). Colored heat maps 18 obtained from MATLAB were warped and overlayed on the textured mesh 16 using Photoshop CS6 Extended (Adobe, Calif., USA) to create a final image as seen in FIG. 2.

Monte Carlo simulations were performed with an open-source Monte Carlo command line application (version 2.0.1). In order to assess penetration depth for a variety of adipose layer thicknesses, sets of simulations were performed with adipose ranging in thickness from 10 mm to 25 mm in 5 mm increments. Fluence was obtained from two separate, 1-million-photon simulations of steady-state photon migration in a three-layered, semi-infinite geometry. The source locations for the two simulations were separated by 22 mm and the fluence results at each bin location were multiplied together to obtain a probability density of detection for a 22 mm source-detector pair. The three layered geometry was chosen to represent an upper skin layer (2 mm), a middle adipose layer (10-30 mm), and a bottom layer of muscle/viscera (1000 mm). The optical properties used in our simulations describe the behavior of light at 800 nm and were readily available from previous studies. In particular, for skin, adipose, and muscle: pa values were 0.025, 0.004, and 0.07 mm$^{-1}$; $\mu_s'$ values were 2.5, 1.9, and 0.7 mm$^{-1}$; g values were 0.8, 0.8, 0.95; and n was fixed at 1.4 for all three tissue types.

Figure 3:
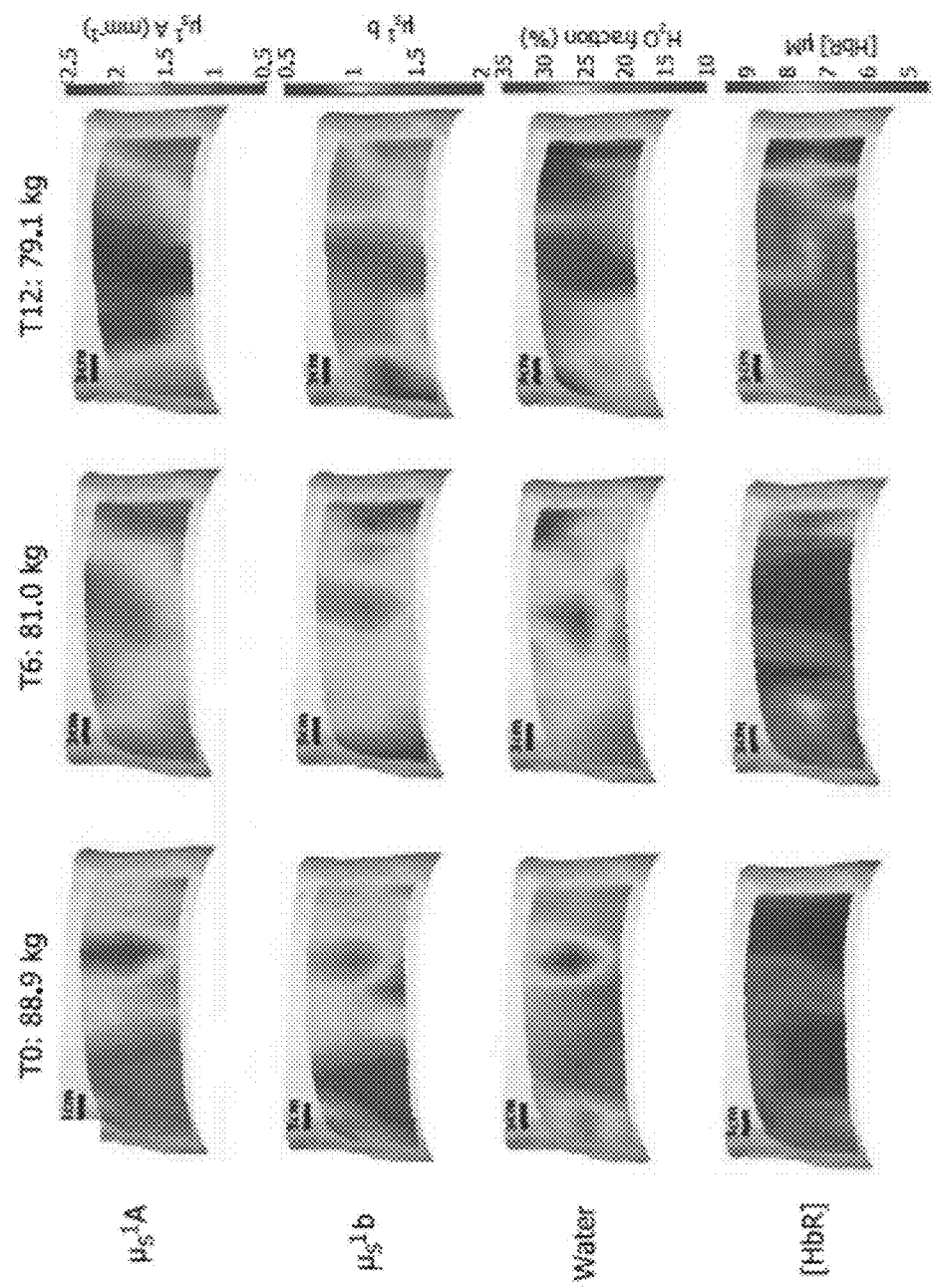
FIG. 3 is a series of images of DOSI parameters in one subject overlayed on three dimensional images of a representative abdomen along with a corresponding measured weight at each respective time is also shown. Row (A) shows a series of images of the $\mu_s'$ A parameter at each respective time. Row (B) shows a series of images of $\mu_s'$ b parameter at each respective time. Row (C) shows a series of images of the water fraction at each respective time. Row (D) shows a series of images of the [HbR] at each respective time.

Serial images of DOSI parameters in one male subject overlayed on 3-D images of a representative abdomen are seen in FIG. 3. FIG. 3 specifically shows sequential images of four parameters in one representative male subject, with corresponding weights shown above. Qualitative analysis of images from this subject demonstrates a gradient in A, with higher baseline values measured in proximity to the abdominal midline, corresponding to areas of thicker subcutaneous AT. Measurement locations in the upper row tend to exhibit higher values of A, and larger increases in A. Both water fraction and [HbR] appear to increase diffusely, particularly in the lateral measurement locations. Corresponding measured weight at each respective time point is also shown. Row (A) shows serial images of $\mu_s'$ A parameter, row (B) shows $\mu_s'$ b, row (C) shows tissue water fraction, and row (D) shows [HbR]. It should be noted however that the heat maps shown in FIG. 3 have been overlayed onto a representative three dimensional abdominal image for visualization purposes only, and that these images do not represent subject abdominal shape or contour.

Figure 5:
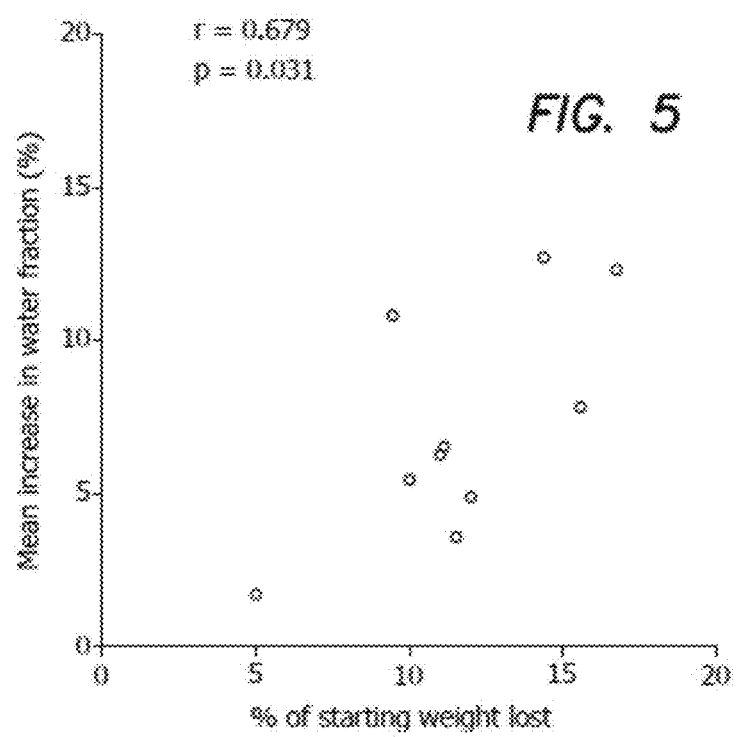
FIG. 5 is a correlation plot graph of mean increase in water fraction percentage versus percentage of starting weight loss for each subject from T0 to T12.

Statistical analysis was performed using R (R Core Team (2014). R: A language and environment for statistical computing. R Foundation for Statistical Computing, Vienna, Austria.) Optical and ultrasound data were analyzed using the lme4 package (version 1.1-7) for computation of linear mixed-effects model. The basic model used was of the following form:

$$Y_{ij} = \beta_0 + \beta_1(X_i) + b_{0ij} + b_{1ij}(X_{ij}) + b_{2ik} + b_{3ik}(X_{ik}) + \varepsilon$$

$$i=1,2,3 \; j=1,2 \ldots 10 \; k=1,2 \ldots 30 \quad (1)$$

where $X_i$ is the effect of calorie restriction (CR), $X_{ij}$ is the effect of CR (i=1-3 levels) for individual subjects (j=1-10), and $X_{ik}$ is the effect of CR for individual positions (k=1-30). $Y_{ij}$ describes the value of an outcome variable for subject j at level of CR i. We modeled CR as a fixed effect and assigning it a categorical factor reflecting duration, with three levels i (T0=0 weeks of CR, T6=6-8 weeks of CR, T12=12-14 weeks of CR). The effect of CR is therefore described by $\beta_1$, with $\beta_0$ corresponding to fixed effect intercept. Model M1 also accounts for random effects of subject and position. Subject random effects are described by intercept $b_{0ij}$ and slope $b_{1ij}$. Position random effects are modeled as intercept $b_{2ik}$ and slope $b_{3ik}$. For each outcome, a value for $\beta_1$ for each level of CR and corresponding p-values are reported. If M1 revealed significant effects of CR on a given outcome variable, model output was used to perform Tukey's contrasts for multiple comparisons between mean values for all subjects at the three measurement sessions, as shown in FIG. 5 and described in the results. Outcomes evaluated using this model included A, b, [Hb02], [HbR], [THb], st02, water content, and lipid content. Model assumptions (linearity and normality) for each outcome was tested by visually inspecting plots of model residuals against fitted values, and by assessment of Q-Q plots respectively.

Prior to any model analysis, DOSI measurements at two points were excluded from analysis due to unphysical values of absorption and scattering, likely a result of improper probe contact. Additionally, 11 measurements from one session (T0) in subject 9 were missing due to instrument malfunction. Pearson Product-Moment Correlation analysis was used to test the mean change in each optical parameter from T0-T12 against the percentage of starting weight lost by each participant.

The effect of CR on weight, abdominal circumference, and blood pressure was tested by Friedman's test and post-hoc pairwise Wilcoxon rank-signed tests with Bonferroni correction.

Results

Mean weight loss for the subjects was larger between T0 and T6 (−7.9 kg) than between T6 and T12 (−4.4 kg). From T0 to T12, the mean reduction in weight for the subjects was 11.7±1.1% (SE) of starting weight. Systolic blood pressure declined by 8 mm Hg between T0 and T6 (adj. p=0.017). Mean tissue thickness at T0 was 3.3 cm, and changed significantly at both T6 and T12 (T6-T0=0.3±0.1 cm, adj. p<0.001, T12-T0=0.5±0.1 cm, adj. p<0.001, T12-T6=0.3±0.1 cm, adj. p<0.001). In terms of position, the subcutaneous fat layer was consistently thicker at positions closer to the midline. Simulation of photon penetration revealed a mean penetration depth of 5-6 mm in AT, with less than 4% signal contribution from tissue more than 1.0 cm deep At each measurement point along the grid 14 for each subject 12, two parameters related to optical scattering were obtained by measuring reduced scattering coefficients at all four wavelengths, according to equation 2:

$$\mu'_s = A\left(\frac{\lambda}{500\text{ nm}}\right)^b \quad (2)$$

Figure 4A:
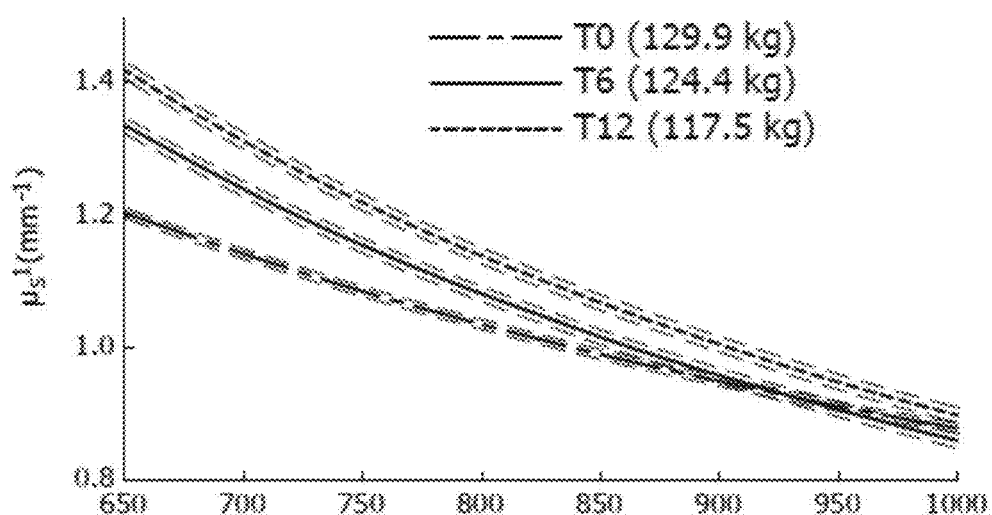
FIG. 4A is a line graph of $\mu_s'$ ($mm^{-1}$) versus wavelength in nm of the mean+/−SD over 29 measurement points of a subject at T0 (black), T6 (magenta), and T12 (green).

Here, b is the unitless "slope" parameter which describes the dependence of scattering on wavelength, while A is a factor in $mm^{-1}$ units corresponding to amplitude of NIR scattering. The $\lambda$ term is the wavelength at which $\mu_s'$ is measured, and the 500 nm in the denominator is a reference wavelength used for normalization. In FIG. 4A, average scattering spectra in a single subject at all measurement sessions are shown. Here, there is both an upward shift in the spectrum with weight loss, as well as a steepening of the curve with respect to wavelength. These observations would therefore constitute an increase in A and a decrease in b.

Figure 6A:
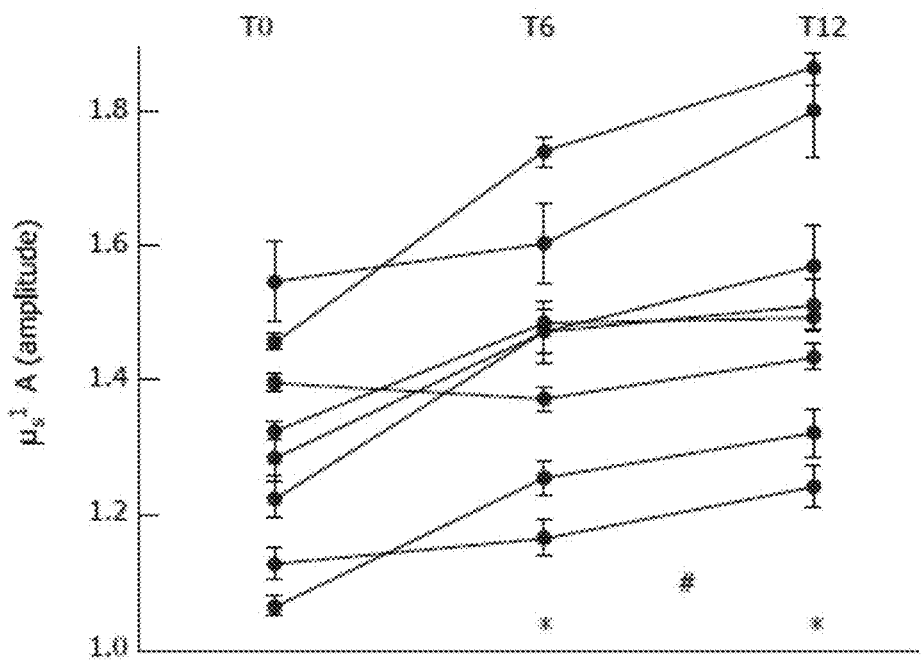
FIG. 6A is a line graph of the measured $\mu_s'$ A scattering parameter versus time for each subject at T0, T6, and T12.
Figure 6B:
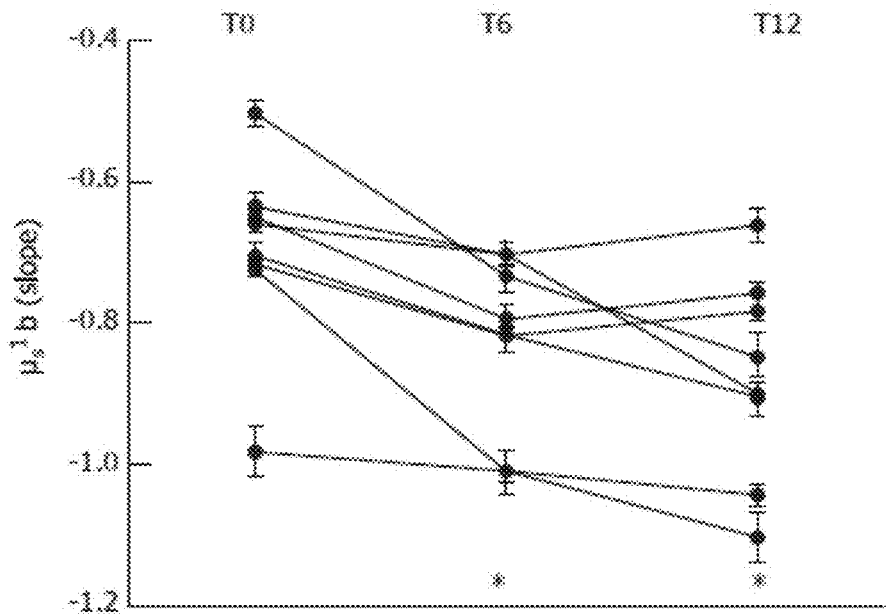
FIG. 6B is a line graph of the measured $\mu_s'$ b scattering parameter versus time for each subject at T0, T6, and T12.

From T0 to T12, A increased by 17.0±8.4% (mean±SD) and ranged from +2.9% to +28.7%. The mean b parameter change was −24.4±20.9%, ranging from +1.0% to −68.5%. A was significantly higher at both T6 as seen in FIG. 6A where T6−T0=0.15±0.04 $mm^{-1}$, adj. p=0.002) and T12 (T12−T6=0.08±0.03 $mm^{-1}$, adj. p=0.007, T12−T0=0.23±0.04 $mm^{-1}$, adj. p<0.001). The b parameter was significantly more negative at T6 and T12 than T0 as seen in FIG. 6B where T6−T0=−0.12±0.03, adj. p=0.001, T12−T6=−0.06±0.02, adj. p=0.040, T12−T0=−0.17±0.04, adj. p<0.001). Both parameters changed more between T0 and T6 than between T6 and T12.

Figure 4B:
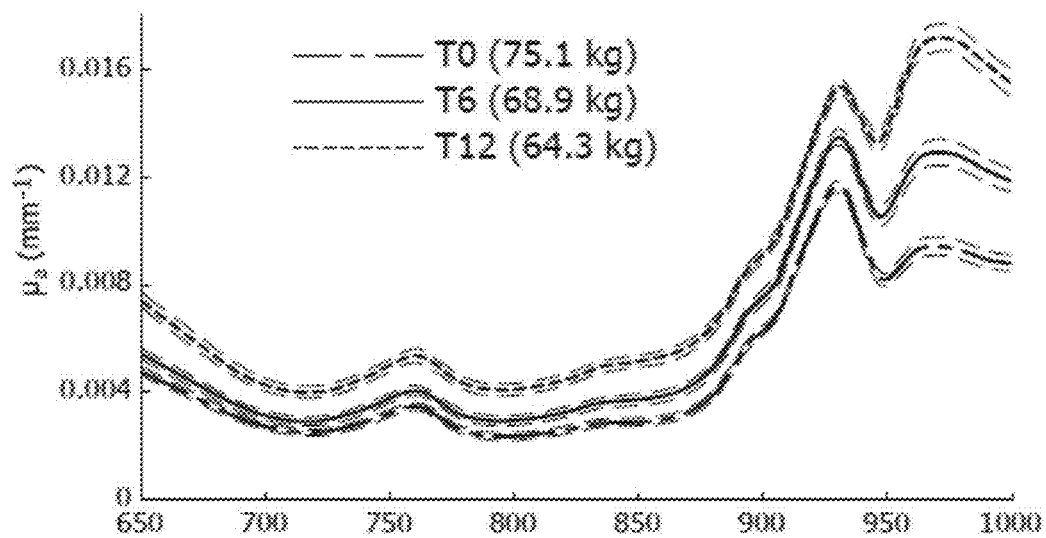
FIG. 4B is a line graph of $\mu_a'$ (mm-1) versus wavelength in nm of the mean+/−SD over 30 measurement points of a subject at T0 (black), T6 (magenta), and T12 (green).
Figure 6C:
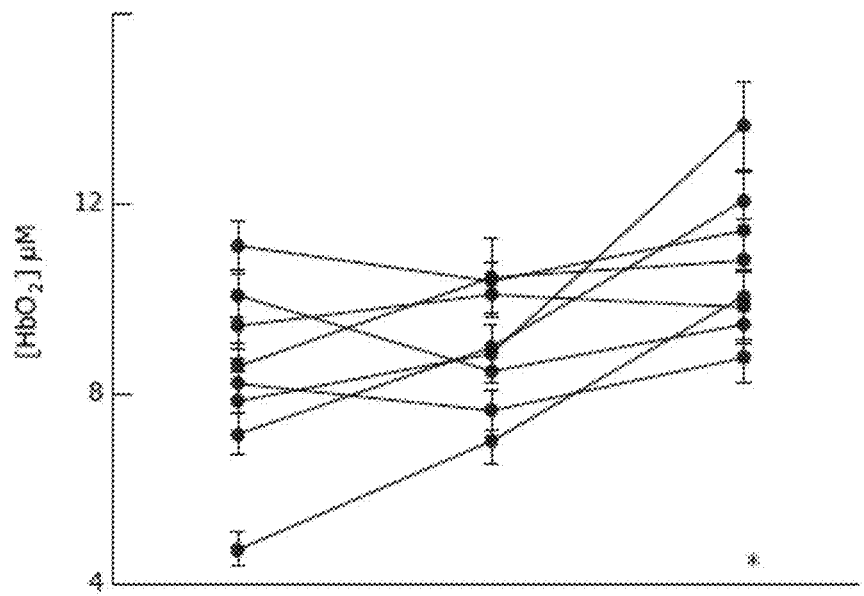
FIG. 6C is a line graph of the measured HbO2 versus time for each subject at T0, T6, and T12.
Figure 6D:
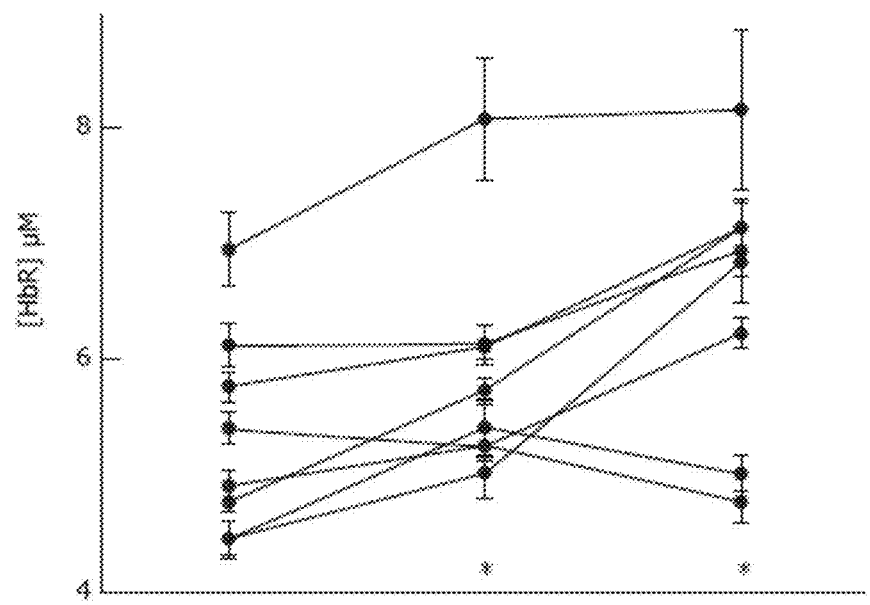
FIG. 6D is a line graph of the measured HbR versus time for each subject at T0, T6, and T12.
Figure 6E:
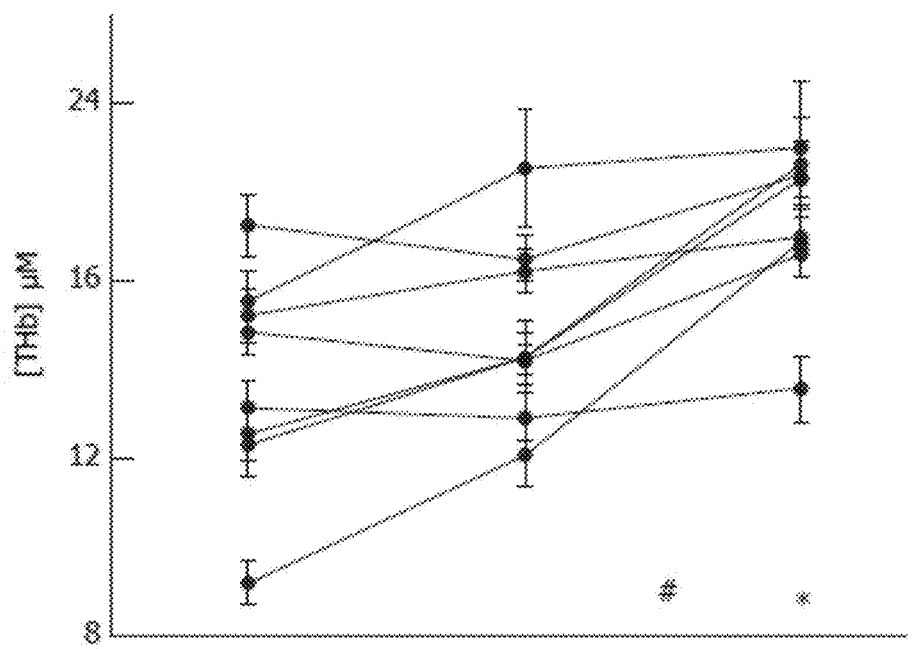
FIG. 6E is a line graph of the measured THb versus time for each subject at T0, T6, and T12.
Figure 6F:
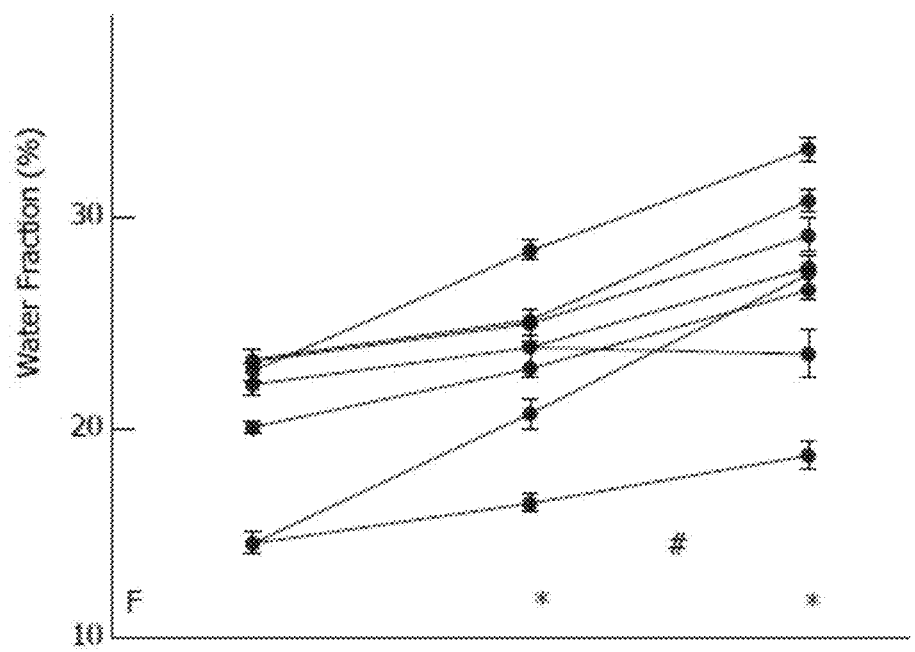
FIG. 6F is a line graph of the measured water fraction percentage versus time for each subject at T0, T6, and T12.

Inspection of absorption spectra measured in individuals revealed progressive upward shifts in the 950-1000 nm range where water is the primary absorber as shown in one representative subject in FIG. 4B. [HbOz] was significantly higher at T12 than T0 as seen in FIG. 6C where T12−T0=2.0±0.8 µM, adj. p=0.019. The mean [HbR] was higher at T12 and T6 than T0 as seen in FIG. 6D where T6−T0=0.6±0.1 µM, adj. p<0.001, T12−T0=1.1±0.3 µM, adj. p<0.001, T12−T6=0.5±0.2 µM, adj. p=0.051. [THb] was higher at T12 than at both T6 and T0 as seen in FIG. 6E where T12−T0=3.2±0.8 µM, adj. p<0.001, T12−T6=2.1±0.8 µM, adj. p=0.026. Finally, the mean tissue water fraction increased from T0 to T6 as seen in FIG. 4F where T6−T0=3.4±1.0%, adj. p=0.003), and from T6 to T12 (T12−T6=3.9±0.6%, adj. p<0.001, T12−T0=7.2±1.1%, adj. p<0.001). No significant associations were found between CR and $stO_2$ or lipid content.

A significant Pearson correlation was found between the magnitude of weight loss and the increase in tissue water content in individual subjects between T0 and T12 as seen in FIG. 5 where r=0.679 and p=0.031.

Discussion

It is known that adipocyte size is dynamic, and that it is positively associated with degree of obesity, as well as fasting insulin levels. A recent study of twins non-concordant for obesity showed that increased weight correlates with larger adipocytes, with or without AT hyperplasia. The response of adipocytes to weight loss interventions has also been observed experimentally. A study in humans has shown that individuals subjected to 12 weeks of a very low calorie diet (<3400 kJ/day) show adipocyte volume reductions on the order of 15-20%. Over this time scale, it is unlikely that a change in subcutaneous AT cell number would be observed, although AT hyperplasia is seen in obesity. It has also been observed that weight loss of 5% of total body weight is sufficient to reduce adipocyte size in severely obese women.

Based on the magnitude of weight loss observed in our study (11.7±3.4% of starting weight, T0 to T12) and the time course of the measurements, it is likely that the increases in NIR scattering amplitude (mean+17.0% from T0 to T12) observed are related to a reduction in subcutaneous adipocyte size. In the NIR range (650-1000 nm), light scattering parameters "A" and "b" correspond to the distributions of density and size of scattering particles, respectively, that are comparable in dimension to the optical wavelength. Therefore, the increase in A could be the result of a higher AT sub-cellular organelle density occurring with adipocyte shrinkage. Our observation that the scattering slope parameter (b), reflecting the size distribution of scattering particles, increased in magnitude is also consistent with this interpretation. Thus, on average, there appears to be a higher density and reduced volume of AT scattering particles with CR.

The specific cellular or extracellular components corresponding to these scattering particles cannot be determined with confidence. However, it is likely that one component is the increased density of membrane-bound organelles, such as vesicles or mitochondria. Indeed, others have found a relationship between mitochondrial content and NIR scattering. Other possibilities include an increased number of multilocular lipid droplets, a feature of beige adipocytes, or higher rates of adipocyte pinocytosis. To determine the precise source of the observed scattering changes, further studies incorporating histology and microscopy are needed. Nevertheless, to our knowledge, these findings represent the first in vivo characterization of NIR scattering properties of AT in a physiological context, and suggest potential utility of such measurements in studies of AT biology.

Analysis of absorption spectra revealed that CR is associated with significant increases in tissue [HbOz], [HbR], [THb], and water fraction, which reflect perfusion, $O_2$ delivery, and hydration. It is known that obesity suppresses AT blood flow at rest, and blunts the postprandial increase in flow, but the implications of this reduction are not fully known. Interestingly, subcutaneous AT $P_{O2}$ has been found to be elevated in obesity by direct measurement, possibly reflecting an $O_2$ extraction deficit. While subcutaneous AT $O_2$ consumption is low compared to other tissues, there is evidence for the relevance of AT hypoxia in the progression of obesity. Furthermore, as described previously, increased oxidative capacity is a feature of brown and beige adipocytes, both of which are associated with improvements in metabolic status. Much about the relationship between diet status, inflammation, and AT metabolism in humans is unknown, largely due to difficulties involved in measuring AT blood flow and $P_{O2}$.

While DOSI does not directly measure these quantities, the changes observed performing the current method suggest that subcutaneous AT responds to weight loss with an increase in $O_2$ extraction ([HbR]), and water content at the bulk tissue level. Weight loss by CR has been shown to decrease total body water content, with an increase in the ratio of extracellular to intracellular water, partly due to the early mobilization of glycogen stores. There is comparatively little known about AT hydration status. A 2003 study used skin surface measurements of dielectric constant to show that that subcutaneous AT water content increases with weight loss by CR. The authors attributed this increase to higher blood flow and nutrient delivery, and also correlated it with an improvement in insulin sensitivity. The fact that we observed an increase in AT [THb] along with water content would seem to support this previous conclusion. While we cannot comment on the relative contributions of extracellular versus intracellular water to the overall increase, DOSI may be sensitive to compartment-specific hydration by resolution of water binding states. Finally, there was a significant correlation within subjects between the percentage of weight lost and the mean increase in water fraction from T0 to T12, suggesting that AT water content could be a useful biomarker for the effectiveness of weight loss interventions.

Because [HbR] changes are known to be a consequence of $O_2$ extraction, the observed [HbR] increase likely reflects enhanced AT $O_2$ extraction. This is consistent with our observation of changes in A and b scattering parameters that suggest a reduction in adipocyte size with weight loss. Adipocyte shrinkage is thought to reduce the $O_2$ diffusion distance to mitochondria, potentiating extraction. However, there are many other factors that influence AT $O_2$ flux. For example, recent data obtained from mice show that an early effect of a high fat diet is increased AT $O_2$ consumption driven by mitochondrial uncoupling. This leads to relative AT hypoxia and HIF-1α mediated inflammation, a phenomenon implicated in insulin resistance. Our measurements of increased [HbR] with CR seem to be in contradiction with these findings, but only if the increased [HbR] is reflective of an increase in individual adipocyte $O_2$ extraction. To resolve this issue would require a measurement of intrinsic AT cellular $O_2$ consumption, as has been done recently using related optical techniques in human skin.

To verify that detected signals were derived primarily from subcutaneous AT and not underlying abdominal musculature, numerical simulations of light propagation in tissue were performed using Monte Carlo techniques. Simulations reveal that the distribution of photon paths using our exact probe geometry and wavelengths have a mean interrogation depth of ~5-6 mm with less than 4% of the total detected photons visiting the muscle layer when adipose thickness was 10 mm. Given that the measured values of subcutaneous AT thickness were always greater than 10 mm, we expect negligible contribution to DOSI signals from deeper tissue components when taking all 30 spatial locations into account. Nevertheless, some of the detected signals may include minor contributions from underlying abdominal wall musculature in extreme lateral measurement locations.

These results suggest that DOSI is sensitive to AT structural and metabolic changes during CR. Our data demonstrates that DOSI-detected changes in AT optical properties are consistent with existing hypotheses on the response of AT to CR and weight loss. DOSI or similar techniques may contribute to a fuller understanding of AT physiology in various metabolic states, and may constitute a new bedside tool for monitoring AT metabolism and composition. Additionally, considering that the magnitude of weight loss seen by performing the current method was associated with significant reduction in blood pressure (systolic: −9±4 mm Hg), it is possible that the changes we have observed in adipose light-tissue interactions may correlate with improvements in vascular disease risk.

In summary, DOSI for monitoring of subcutaneous fat is advantageous because:
a. It provides both structural and functional information about tissue
b. It is non-invasive and requires no ionizing radiation
c. The technology is portable
d. Measurements can be done repeatedly with no additional discomfort
e. Near-Infrared light is well suited to the assessment of superficial low absorbing tissues such as subcutaneous fat.

DOSI may contribute to a fuller understanding of AT biology in various metabolic states, and may constitute a new bedside tool for monitoring AT metabolism and composition generally. While DOSI is not capable of the spatial resolution of MRI, it offers advantages in quantitation, spectral information content, ease of application and cost. DOSI and similar technologies might be used to guide therapeutic interventions such as diet, exercise, and medication by assessing their impact on AT physiology quantitatively and longitudinally.

Many alterations and modifications may be made by those having ordinary skill in the art without departing from the spirit and scope of the embodiments. Therefore, it must be understood that the illustrated embodiment has been set forth only for the purposes of example and that it should not be taken as limiting the embodiments as defined by the following embodiments and its various embodiments.

Therefore, it must be understood that the illustrated embodiment has been set forth only for the purposes of example and that it should not be taken as limiting the embodiments as defined by the following claims. For example, notwithstanding the fact that the elements of a claim are set forth below in a certain combination, it must be expressly understood that the embodiments includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the embodiments is explicitly contemplated as within the scope of the embodiments.

The words used in this specification to describe the various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the embodiments.

We claim:

1. A method for measuring dynamic changes in subcutaneous white adipose tissue metabolism in vivo in a patient during a weight loss treatment comprising:
    identifying a plurality of test points on the abdominal region of a patient;
    generating a diffuse optical spectroscopic image (DOSI) using near-infrared light at each of plurality of test points;
    generating a measurement of tissue reduced scattering ($\mu_s'$) and absorption ($\mu_a$) coefficients at each of the plurality of test points in the diffuse optical spectroscopic image (DOSI);
    calculating a plurality of chromophore concentrations from the measured tissue absorption coefficients at each of the plurality of test points in the diffuse optical spectroscopic image (DOSI);
    deriving structural information about the subcutaneous white adipose tissue from the measured reduced scattering coefficients at each of the plurality of test points in the diffuse optical spectroscopic image (DOSI);
    repeating at intervals during the weight loss treatment the steps of identifying a plurality of test points on the abdominal region of a patient, generating a diffuse optical spectroscopic image (DOSI) using near-infrared light at each of plurality of test points, generating a measurement of tissue absorption ($\mu_a$) and reduced scattering ($\mu_s'$) coefficients at each of the plurality of test points in the diffuse optical spectroscopic image (DOSI), calculating the concentrations of a plurality of chromophores from the measured tissue absorption ($\mu_a$) coefficient, and deriving structural information of the subcutaneous white adipose tissue from the measured tissue reduced scattering ($\mu_s'$) coefficients at each of the plurality of test points in the diffuse optical spectroscopic image (DOSI);
    comparing the calculated concentrations of the plurality of chromophores and derived structural information of the subcutaneous white adipose tissue obtained at each of the repeated intervals during the weight loss treatment to monitor changes in previously calculated chromophore concentrations and derived structural information of the subcutaneous white adipose tissue during the weight loss treatment; and
    guiding therapeutic interventions including diet, exercise, and medication based on the monitored changes in the concentrations of the plurality of chromophores and structural information of the subcutaneous white adipose tissue during the weight loss treatment.

2. The method of claim 1 where generating a diffuse optical spectroscopic image (DOSI) using near-infrared light at each of the plurality of test points comprises placing at least one photodetector and at least one light source to provide multiple wavelengths of light in the near-infrared (650-1000 nm) at each of the plurality of test points.

3. The method of claim 1 where generating a diffuse optical spectroscopic image (DOSI) using near-infrared light at each of plurality of test points comprises combining frequency domain photon migration (FDPM) sensing at a plurality of discrete wavelengths with broadband diffuse reflectance spectroscopy (DRS) to determine broadband absorption and scattering to allow for calculation of concentrations of chromophores in tissue at the plurality of test points.

4. The method of claim 1 where generating a diffuse optical spectroscopic image (DOSI) using near-infrared light at each of plurality of test points comprises plotting a plurality of DOSI data collected at each of the plurality of test points to create a heat map representing the concentration of at least one of the plurality of chromophores in the subcutaneous white adipose tissue structure,
    wherein plotting a plurality of DOSI data collected at each of the plurality of test points to create a heat map comprises:
    plotting the plurality of DOSI data at grid coordinates corresponding to the plurality of test points;
    interpolating between each of the grid coordinates onto the heat map; and
    overlaying the heat map onto a three dimensional textured mesh of a representative abdomen of a patient to create a processed image.

5. The method of claim 3 where combining frequency-domain photon migration (FDPM) sensing at a plurality of discrete wavelengths with broadband diffuse reflectance spectroscopy (DRS) to determine broadband absorption and scattering to allow for calculation of concentrations of chromophores in tissue at the plurality of test points comprises combining the measured values obtained from the frequency domain photon migration (FDPM) sensing with the measured values obtained from broadband diffuse reflectance spectroscopy (DRS) to determine the tissue absorption coefficient ($\mu_a$) and the reduced scattering coefficient ($\mu_s'$) over a wavelength spectrum for each of the plurality of test points including 650-1000 nm.

6. The method of claim 1 where calculating the concentrations of a plurality chromophores from the measured tissue absorption coefficients comprises calculating concentrations of oxyhemoglobin ($HbO_2$), deoxyhemoglobin (HbR), total hemoglobin (THb), and fractions of water content and lipid content, and where deriving structural information about the subcutaneous white adipose tissue from the measured reduced scattering coefficients comprises calculating scattering amplitude (A) and slope (b) from the wavelength dependent function of reduced scattering for near-infrared light in biological tissues.

7. The method of claim 6 further comprising obtaining an oxygen saturation ($StO_2$) and a tissue optical index (TOI) related to the patient, wherein the oxygen saturation is the ratio of oxyhemoglobin to total hemoglobin, and wherein the tissue optical index is the product of the water fraction and deoxyhemoglobin divided by the lipid fraction, the oxygen saturation and tissue optical index representing indices of metabolic activity of the patient.

8. The method of claim 6 further comprising comparing the measured tissue reduced scattering coefficients ($\mu_s'$) obtained at each of the repeated intervals during the weight loss treatment to determine if the tissue reduced scattering coefficient has changed, wherein an increase in the scattering amplitude (A) is indicative of a higher density of scatterers and an increase in slope (b) is indicative of a reduced size of scatterers within the measured volume of subcutaneous white adipose tissue within the patient.

9. The method of claim 8 further comprising guiding therapeutic interventions including diet, exercise, and medication based on if a change in the tissue reduced scattering coefficients has been determined.

10. The method of claim 8 further comprising assessing improvements in vascular disease risk observed in the patient based on if a determined increase in the tissue reduced scattering coefficient has been determined.

\* \* \* \* \*